United States Patent [19]

Ogawa

[11] Patent Number: 5,014,716
[45] Date of Patent: May 14, 1991

[54] SPHYGMOMANOMETER AIR CONNECTOR

[75] Inventor: Hiroshi Ogawa, Nagaokakyo, Japan

[73] Assignee: Omron Tateisi Electronics Co., Kyoto, Japan

[21] Appl. No.: 410,887

[22] Filed: Sep. 22, 1989

[30] Foreign Application Priority Data

Sep. 28, 1988 [JP] Japan .................. 63-127669[U]

[51] Int. Cl.⁵ .............................................. A61B 5/02
[52] U.S. Cl. ..................................... 128/685; 137/861; 137/874
[58] Field of Search ............... 128/677, 685; 137/269, 137/861, 874; 73/37

[56] References Cited

FOREIGN PATENT DOCUMENTS 14386 8/1882 Fed. Rep. of Germany ...... 137/861
3117546 10/1982 Fed. Rep. of Germany ...... 128/685

Primary Examiner—William E. Kamm
Assistant Examiner—Scott R. Akers
Attorney, Agent, or Firm—Dickstein, Shapiro & Morin

[57] ABSTRACT

An air connector for use in association with a sphygmomanometer body, comprising an air socket having an air plug acceptor and a pressure measuring air line and an exhaust air line each communicating with the air plug acceptor, an air supply plug removably connected to the air plug acceptor of air socket and provided with an air tube joint at one end thereof and an insert cylinder at the other end, and a control means which is removably connected to the insert cylinder of air supply plug and, upon installation, brings the air supply line of air supply plug into communication with the pressure measuring air line and exhaust air line for blood pressure determination and, upon removal, brings the air supply line of air supply plug selectively into communication with the pressure measuring air line for pressure assay.

3 Claims, 3 Drawing Sheets

SPHYGMOMANOMETER AIR CONNECTOR

BACKGROUND OF THE INVENTION

1. Field of the Invention

The present invention relates to a sphygmomanometer air connector for pneumatic connection between a sphygmomanometer body and a pneumatic cuff.

2. Brief Description of the Prior Art

The sphygmomanometer has a built-in air system including a compression pump, a pressure sensor for detecting the pressure of a pneumatic cuff, a slow-speed exhaust valve and so on. For sphygmomanometry, the air tube of the cuff is connected to the above pneumatic system through an air connector and the cuff is compressed by the compression pump (not shown). In the actual determination of arterial blood pressure, the pneumatic cuff is set on the upper arm of the subject and the air compressed by the compression pump is delivered to the pneumatic cuff to arrest the blood flow in the bracheal artery. Then, in the slow exhaust or deflation stage, the appearance and disappearance of the Korotkoff sounds are detected and the cuff pressure at the appearance of the K sounds is taken as the systolic blood pressure while the cuff pressure at the disappearance of the sounds is regarded as the diastolic pressure.

The sphygmomanometer is subject to the Metric Law which provides that air leaks shall not be more than 4 mmHg in 3 minutes and, as such, is assayed item-by-item by the metric assay authority. When a sphygmomanometer is subjected to this assay with the air system of the sphygmomanometer body connected to the assay air system at the authority, compressed air must be supplied exclusively to the built-into pressure gauge (pressure measuring means) of the sphygmomanometer. For this purpose, it is the usual practice to either plug the exhaust valve or clip the air line of the exhaust valve to block the air flow. However, these procedures are inconvenient in that prior to assay, the cover must be removed from the sphygmomanometer body.

Therefore, the present applicant previously proposed a sphygmomanometer air connector as illustrated in FIG. 5(A) and (B).

This sphygmomanometer air connector comprises, as used in association with a sphygmomanometer body 61, an air socket 65 having a pressure measuring air line 63 and an exhaust air line 64 each communicating with an air plug acceptor 62, a short-length air supply plug 67 [See FIG. 5(B)] which is dismountably connected to the air plug acceptor 62 of said air socket 65 and has an air supply line 66 adapted to communicate, upon installation of the plug 67, with the pressure measuring air line 63 and exhaust air line 64 of said air socket 65, a long-length pressure assay auxiliary plug 69 which is dismountably connected to said air plug acceptor 62 of air socket 65 and upon installation thereof, obstructs said exhaust air line 64 of air socket 65, with its air supply line 68 alone being brought into communication with said pressure measuring air line 63.

In measuring the blood pressure, the short-length air plug 67 illustrated in FIG. 5(B) is inserted into the air socket 65. The air plug 67 is provided with a joint 67a for connection of the air tube of the pneumatic cuff at one end (base) thereof, while the tapered portion 67b at the other end (tip) is abutted against a tapered wall 65a at the plug acceptor 62 of the air socket 65. Upon insertion, the forward end of the air plug 67 is detained short of the position of the exhaust air line 64 and that of the pressure measuring air line 63, with the result that the pressure measuring air line 63 and exhaust air line 64 are brought into communication with the air supply line 66 of the air plug 67. Stated differently, the air system of the sphygmomanometer communicates with the pneumatic cuff. Hence, sphygmomanometry can be executed.

In the pressure assay, the long-length auxiliary plug 69 is inserted into the air socket 65 [See FIG. 5(A)]. That is to say, the air plug 67 fitted into the air socket 65 is disconnected and instead, the auxiliary plug 69 is inserted. The auxiliary plug 69 is formed at one end (base) thereof with a joint 69a' for connection of the air tube of the assay pneumatic system and at the other end a tapered portion 69b complementary with the taper 65a of the air socket 65, with a forward reduced-diameter part 69c of said tapered portion 69b being provided with an opening 69d which communicates with the air supply line 68 and a closure rubber piece 69e being attached to the forward end of said reduced-diameter part 69c. Therefore, upon insertion of the auxiliary plug 69, the closure rubber piece 69e obstructs the exhaust air line 64 of air socket 65, while the opening 69d is brought into communication with the pressure measuring air line 63. Stated differently, only the exhaust air line 64 of the air socket 65 is obstructed. Therefore, the pressure assay of the sphygmomanometer can be properly executed.

In the above sphygmomanometer air connector which was previously proposed by the present applicant, sphygmomanometry and pressure assay can be selectively performed by the mere procedure of inserting either the air plug or the auxiliary plug into the air socket exposed on the surface of a sphygmomanometer body. Therefore, the troublesome procedure of removing the cover from the sphygmomanometer body for each blood pressure determination or pressure assay and reinstalling the cover after the determination or assay was overcome.

However, this sphygmomanometer air connector requires an auxiliary plug for pressure assay in addition to the air plug for blood pressure determination. Therefore, the product sphygmomanometer must be supplied with the auxiliary plug, which is unnecessary for blood pressure determination, as an attachment, thus contributing to an increased product price but an increased risk of missing the auxiliary plug which is not frequently used.

SUMMARY OF THE INVENTION

It is an object of the present invention is to solve the above-mentioned problems and provide a convenient sphygmomanometer air connector having a single air plug member which can serve the dual purpose of sphygmomanometry and pressure assay. Other objects and advantages of the present invention will become apparent as the following description of the invention proceeds.

The sphygmomanometer air connector of the present invention comprises, as installed in association with a sphygmomanometer body, an air socket having an air plug acceptor and a pressure measuring air line and an exhaust air line each communicating with said air plug acceptor, an air supply plug dismountably connected to the air plug acceptor of said air socket and having an air tube joint at one end thereof and an insert cylinder member at the other end, and a control means which is dismountably connected to the insert cylinder of said air supply plug and, upon installation, brings the air supply line of said air supply plug into communication with said pressure measuring air line and exhaust air line and, upon removal, brings the air supply line of said air supply plug into communication with said pressure measuring air line.

In the sphygmomanometer air connector thus constructed, a cylindrical control means having a thread on its inner circumferential surface fits over the insert cylinder having a mating thread and locked in position as the threads are meshed with each other. The air tube of a pneumatic cuff is connected to the joint at the other end of the air plug. In normal condition, the forward end of the insert cylinder of the air plug enters into the air plug acceptor of the air socket and is locked in position by the O-ring of the air socket. In this inserted condition, the end face of the control means (cylinder) is abutted against the open end of the air socket (the end face exposed from the sphygmomanometer body). Therefore, the depth of insertion of the insert cylinder is controlled "shallow" by the length of the control means (cylindrical member) so that the forward end of the insert cylinder is positioned behind the opening of the pressure measuring air line. Furthermore, since the outer diameter of the insert cylinder is smaller than the diameter of the plug acceptor, there is a clearance between the outer peripheral surface of the insert cylinder and the opening of the exhaust air line. Therefore, in normal condition, the pneumatic system of the sphygmomanometer (blood measuring air line and exhaust air line) communicates with the air supply line of the air plug. Stated differently, the pneumatic system of the sphygmomanometer body is communicating with the pneumatic cuff, thus enabling execution of blood pressure determination.

For pressure assay, the control means is threaded off from the air plug. In this state, the insert cylinder is inserted into the plug acceptor of the air socket. Since the insert cylinder by now has no control means, it can be inserted deeper into the plug acceptor so that the forward end of the insert cylinder sealingly engages the opening of the pressure measuring air line of the air socket. Therefore, the air supply line of the air plug communicates selectively with the pressure measuring air line of the sphygmomanometer alone, with its exhaust air line not communicating with the air supply line of the air plug. Stated differently, only the exhaust air line is obstructed. By connecting the air tube of the assay pneumatic system to the joint at the other end of the air plug in the above condition, a pressure assay of the sphygmomanometer can be executed.

Thus, simply by detaching the control means from the air plug for pressure assay, the single air plug can be used for both sphygmomanometry and pressure assay.

DETAILED DESCRIPTION OF THE PREFERRED EMBODIMENT

Figure 1:
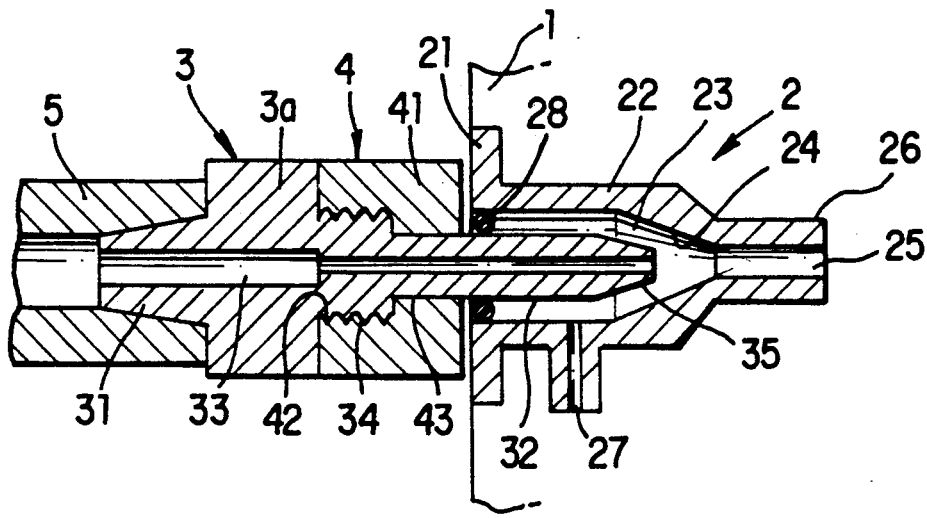
FIG. 1 is a sectional elevation view showing a sphygmomanometer air connector embodying the principle of the present invention in the condition ready for sphygmomanometric determination.

FIG. 1 is a sectional elevation view showing a specific embodiment of the sphygmomanometer air connector according to the present invention.

This sphygmomanometer air connector comprises an air socket 2, which is attached to a sphygmomanometer body 1, an air plug 3 which is removably inserted into said air socket 2, and a control means 4 which is dismountably connected to said air plug 3 and adapted to control the depth of insertion of the air plug 2 with respect to the air socket 1.

The air socket 2 is a generally cylindrical hollow element 22 having a flange 21 at one open end and defining a bore which serves as a plug socket 23, with the inner circumference of said cylinder 22 being progressively reduced toward the other end to define a tapered bore 24 in contiguity with the first-mentioned bore. Formed further in continuity with said tapered bore 24 is a reduced-diameter bore 26 which serves as a pressure measuring air line 25. In addition, an exhaust air line 27 is formed through the wall of the cylinder 22 at an appropriate position as illustrated. This air socket 2 is mounted on the sphygmomanometer body 1 with said flange 21 extending out.

The above-mentioned air plug 3 comprises a flat cylinder 3a formed with a tapered air tube joint 31 at one end (base) and an insert cylinder 32 which is smaller in diameter than said plug acceptor 23 at the other end (tip). Provided in this air plug 3 (cylinder 3a and insert cylinder 32) is an air supply line 33 extending from said one end to said other end. In addition, a thread 34 of expanded diameter is formed at the base of the insert cylinder 32 (on the forward side of the cylinder 3a). Furthermore, the forward end of the insert cylinder 32 is formed with a tapered portion 35 which is complementary with said tapered surface 24 of air socket 2 and the tip of this tapered portion 35 is adapted to sealingly engage with the opening of the pressure measuring air line 25.

Figure 3:
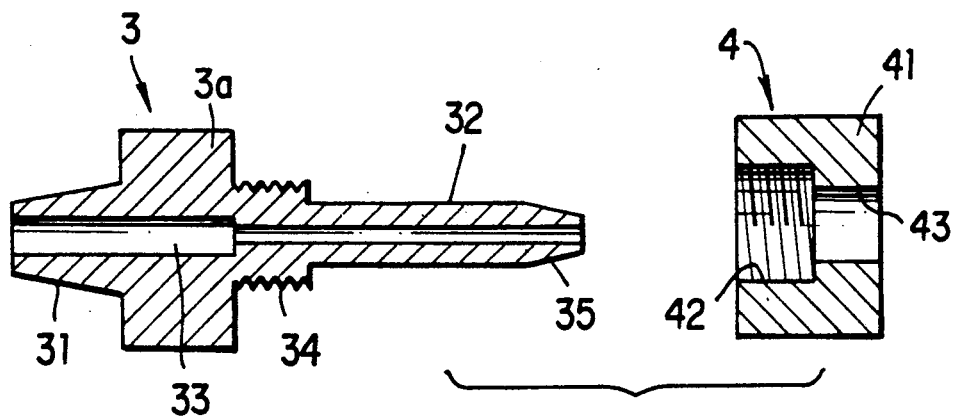
FIG. 3 is a disassembled sectional view showing the air plug and control means of the connector as detached from each other.

The above-mentioned control means 4 comprises a cylindrical element 41 having an outer diameter equal to that of the cylinder 3a of said air plug 3 and a thread 42 adapted to mesh with the thread 34 of said air plug 3. This thread 42 is formed from one end (base) of the cylinder 41 to the middle of its length and the portion of the cylinder 41 which is extending from the end of said thread 42 to the other end (tip) is slightly reduced in inner diameter to define a stop portion for delimiting the forward plane of said thread 34. As shown in the disassembled view of FIG. 3, this control means 4 is removably connected to the insert cylinder 32 of air plug 3 and locked with respect to the air plug 3 as its thread 42 engages the thread 34. In normal condition, the control means 4 is connected to the air plug 3 and the insert cylinder 32 is inserted into the plug acceptor 24 of air socket 2 and locked in position by the O-ring at the opening end of the air socket 2.

Figure 4:
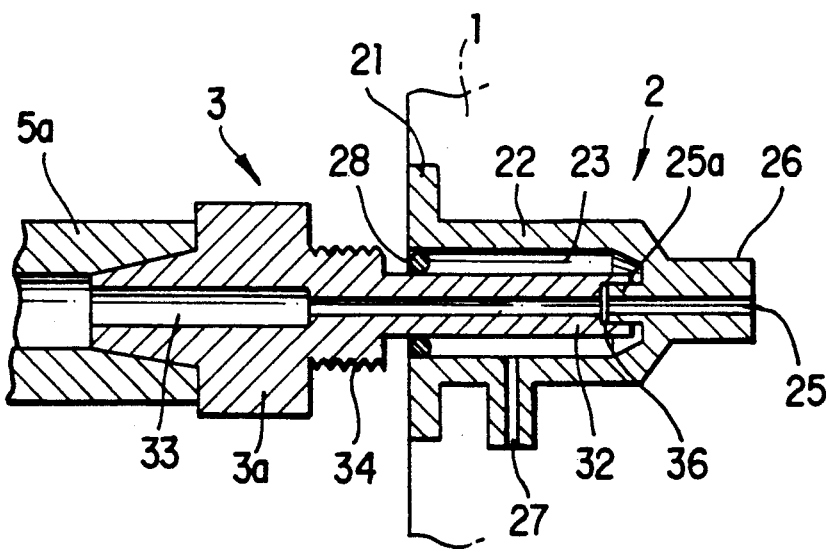
FIG. 4 is a sectional elevation view showing another air connector embodying the principle of the invention.
Figure 5A:
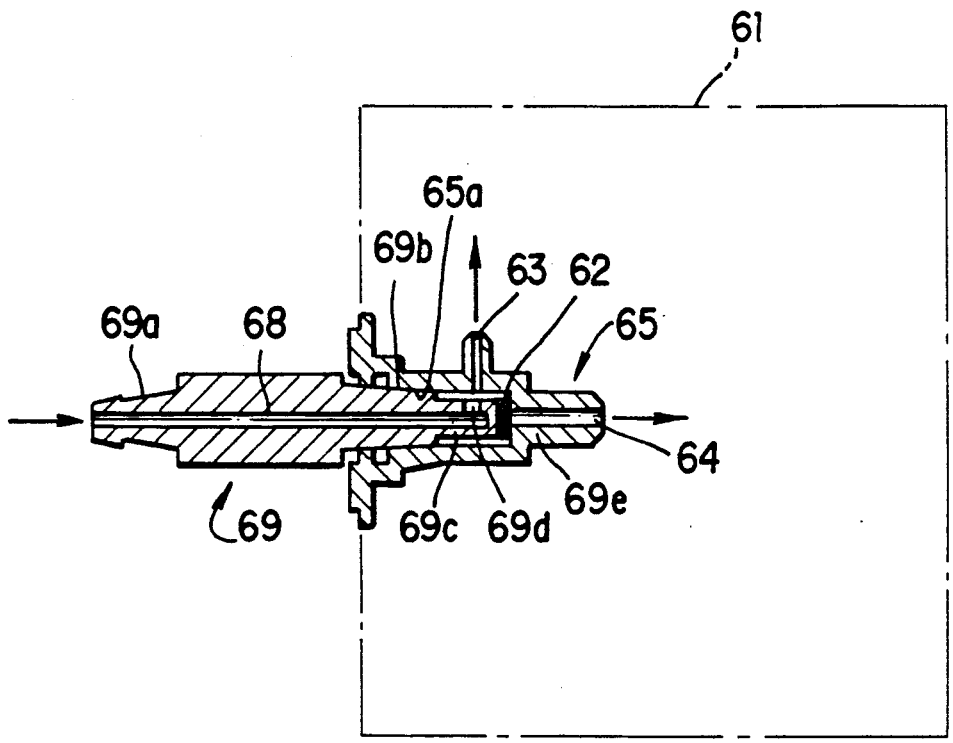
FIG. 5(A) is a sectional elevation view showing the air connector previously proposed by the same applicant in the mode of pressure assay and, FIG. 5(B) is a sectional elevation view showing the same air connector in the mode of sphygmomanometry.
Figure 5B:
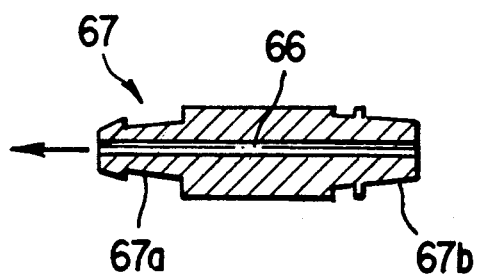

FIG. 4 is a sectional elevation view showing another embodiment of the air connector.

Whereas the embodiment so far described is so constructed that the forward end of the insert cylinder 32 has a tapered portion 35 which is complementary with the tapered portion 24 of the air socket 2, this second embodiment is so constructed that the opening 25a of the pressuring measuring air line 25 of air socket 2 projects inwardly into the plug socket 24 and this projecting opening 25a sealingly engages the tip opening 36 of the insert cylinder 32.

In the normal state of thus-constructed sphygmomanometer air connector, the insert cylinder 32 of the air plug 3 is inserted into the air plug acceptor 23 of the air socket 2 and locked in position by the O-ring of the air socket 2. In this state, the end face (at the forward end) of the control means 4 (cylindrical element) is abutted against the opening end 21 of the air socket 2 (which is the end face projecting from the sphygmomanometer body 1). Therefore, the depth of insertion of the insert cylinder 32 is controlled "shallower" by the length of control means 4 (cylindrical element) (the length of the stop portion 43 of the cylinder 41), so that the forward end of the insert cylinder 32 is set in a position reawardly displaced from the opening of the pressure measuring air line 25. Furthermore, since the outer diameter of the insert cylinder 32 is smaller than the diameter of the plug acceptor of the air socket 2, there is a clearance between the peripheral surface of the insert cylinder 32 and the opening of the exhaust air line 27. Therefore, in the normal condition, the pneumatic system of sphygmomanometer 1 (pressure measuring air line 25 and exhaust air line 27) is communicating with the air supply line 33 of the air plug 3. That is to say, the air system of the sphygmomanometer is communicating with the pneumatic cuff so that sphygmomanometry can be executed.

Figure 2:
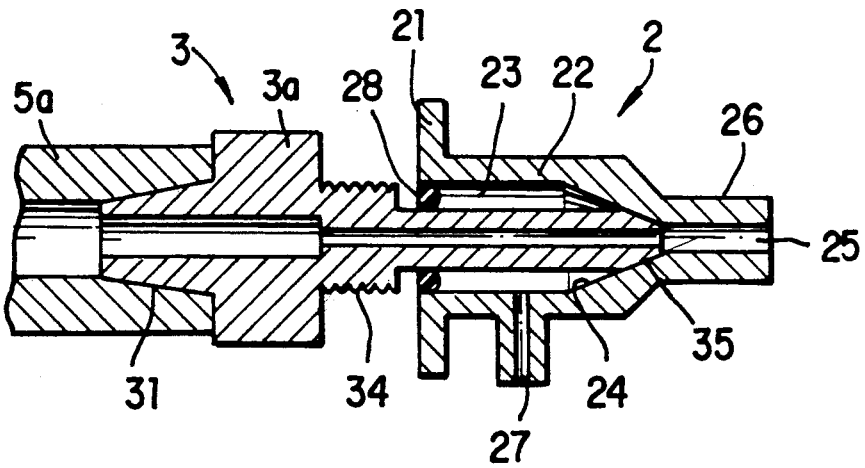
FIG. 2 is a sectional elevation view showing the same connector in the condition ready for sphygmomanometer pressure assay.

In conducting the pressure assay, the control means 5 is threaded off from the air plug 3. In this state, as shown in FIG. 2, the insert cylinder 32 now of the air plug 3 is inserted into the plug acceptor 23 of the air socket 2. Since the insert cylinder 32 now does not carry the control means 4, it enters deep into the plug acceptor 23 until its forward end sealingly engages the open end of the pressure measuring air line 25 of the air socket 2. As a result, the air supply line 33 of air plug 3 communicates only to the pressure measuring air line 25 of sphygmomanometer 1, with its exhaust air line 27 not communicating with the air supply line 33. As the air tube 5a of the assay pneumatic system is connected to the other joint 31 of the air plug 3, the pressure assay of the sphygmomanometer can be executed.

Thus, both sphygmomanometry and pressure assay can be performed using the same single air plug 3, by dismounting the control means 4 from the air plug 3 only for pressure assay.

In accordance with the present invention which as aforesaid, includes a control means for controlling the depth of insertion of the air plug into the air socket, the control means limits said depth of insertion to bring the pressure measuring air line and exhaust air line of the air socket into communication with the air supply line of the air plug for execution of sphygmomanometry. On the other hand, when the air plug without the control means is inserted, the plug can be inserted deeper so that the forward end of the air supply line of the air plug is selectively brought into communication with the pressure measuring air line alone, with the exhaust air line being obstructed, for execution of pressure assay. The present invention, therefore, provides the advantage that the mere mounting and dismounting of a control means with respect to an air plug enables selective execution of blood pressure determination and sphygmomanometer pressure assay.

What is claimed is:

1. An air connector for use in association with a sphygmomanometer body, comprising an air socket having an air plug acceptor and a pressure measuring air line and an exhaust air line each communicating with said air plug acceptor, an air supply plug having an air supply line wherein said air supply plug is removably connected to the air plug acceptor of said air socket and provided with an air tube joint at one end thereof and an insert cylinder at the other end movable within said air plug acceptor to define a first position with said air supply line in communication with said pressure measuring air line and said exhaust air line and a second position with said air supply line in communication only with said pressure measuring air line and a control cylinder which is removably connected to said insert cylinder of said air supply plug for maintaining said insert cylinder in said first position.

2. The air connector of claim 1, wherein said air socket has a tapered bore and wherein a forward end of said insert cylinder is tapered so as to sealingly abut said tapered bore in said air socket.

3. The air connector of claim 1 wherein the opening of said pressure measuring air line of said air socket projects inwardly into said plug acceptor to sealingly engage with a tip opening of said insert cylinder.

* * * * *